United States Patent [19]

Okamura et al.

[11] Patent Number: 5,007,928
[45] Date of Patent: Apr. 16, 1991

[54] INTRAOCULAR IMPLANT HAVING COATING LAYER

[75] Inventors: Moriyuki Okamura, Sagamihara; Ikuo Nakajima, Tokyo; Toshiji Nishiguchi, Kawasaki, all of Japan

[73] Assignee: Canon Kabushiki Kaisha, Tokyo, Japan

[21] Appl. No.: 357,281

[22] Filed: May 26, 1989

[30] Foreign Application Priority Data

May 31, 1988 [JP] Japan ................... 63-133155

[51] Int. Cl.$^5$ ............................................. A61F 2/16
[52] U.S. Cl. ............................................. 623/6; 427/2; 427/40; 427/41
[58] Field of Search ................... 623/6; 427/2, 40, 41; 351/160 R, 160 H, 160

[56] References Cited

U.S. PATENT DOCUMENTS

| 4,143,949 | 3/1979 | Chen | 351/160 H |
| 4,198,714 | 4/1980 | Vensen | 623/6 |
| 4,312,575 | 1/1982 | Peyman et al. | 351/160 H |
| 4,729,914 | 3/1988 | Kliment et al. | 351/160 R X |
| 4,731,078 | 3/1988 | Stoy et al. | 623/6 |
| 4,806,382 | 2/1989 | Goldberg et al. | 623/6 X |

Primary Examiner—Ronald Frinks
Attorney, Agent, or Firm—Fitzpatrick, Cella, Harper & Scinto

[57] ABSTRACT

The intraocular implant comprises a lens substrate and a coating layer with an adhesion layer provided therebetween, the adhesion layer comprising a specific compound.

9 Claims, 1 Drawing Sheet

INTRAOCULAR IMPLANT HAVING COATING LAYER

BACKGROUND OF THE INVENTION

1. Field of the Invention

The present invention relates to an intraocular implant (or artificial substitute lens) having on its surface a coating layer.

2. Related Background Art

Cataracts have been hitherto treated by surgery to remove a lens which had become opaque and insert an artificial lens into the lenticular capsule, and restraining vision after the surgery. At present, such an intraocular implant is prevailingly used in the "in-the-bag system" which is considered to cause less complication that may accompany implantation, i.e., a system in which the intraocular implant is inserted into the "lenticular capsule".

As materials for such intraocular implants, polymethyl methacrylate is mainly used, and on the other hand, as materials for a lens support member called "haptic", polymethyl methacrylate, polyvinylidene fluoride or the like is used.

The intraocular implants are used on condition that they are pemanently fitted in eyeballs, and hence various functions are required to be imparted thereto. The functions to be imparted are exemplified by the hydrophilic nature to prevent corneal cells from being damaged or improves a lens fitted feeling, the ultraviolet absorbency to protect intraocular tissues from harmful near ultraviolet rays which may cause destruction of the tissues, the anti-dissolving property to prevent free monomers in an intraocular implant from dissolving into an eye, and the wear resistance to be required at the time of implantation and after that time.

These functions have been hitherto (i) imparted to the intraocular implant itself, and (ii) imparted to a coating layer provided on the surface of the intraocular implant.

The instance (i) in which the functions are imparted to the intraocular implant itself is hitherto known to include, for example, an example where the intraocular implant is made using HEMA (hydroxyethyl methacrylate) to impart the hydrophilic nature, an example where the intraocular implant is made using PMMA (polymethyl methacrylate) mixed with an ultraviolet-absorbing dye to impart an ultraviolet light screening property, and an example in which the intraocular implant is subjected to plasma treatment in nitrogen gas or argon gas to effect an improvement.

The instance (ii) in which the various functions are imparted to a coating layer provided on the surface of the intraocular implant is hitherto known to include, for example, an example where a plasma-polymerized film of a fluorinated hydrocarbon type is provided on the surface of an intraocular implant to impart thereto the wear resistance and anti-dissolving property.

U.S. Pat. No. 4,312,575 also discloses an intraocular implant having a coating layer formed on the surface thereof by plasma polymerization to impart the anti-dissolving property, and further comprising an ultraviolet-absorbing coloring substance included into the inside of the intraocular implant.

However, in the conventional intraocular implants having a coating layer, in particular, the intraocular implants comprising an intraocular implant lens substrate made of a poor adhesion polymer, no stable adhesion can be attained between the coating layer and lens substrate and also no sufficient longlasting durability can be achieved, so that difficulties have often occurred in permanently fitting intraocular implants.

To improve the adhesion between the coating layer and lens substrate, film formation conditions should be set within the range in which an optimum adhesion can be achieved. In instances where, for example, the coating layer is formed by plasma polymerization. Such formation of the coating layer requires a very delicate control of conditions in preparing intraocular implants, and is accompanied by a number of difficulties. Even if very delicate control of conditions is possible in carrying out the film formation, there is the problem that the surface of the lens substrate may be seriously damaged when a large discharge power is used in carrying out the film formation, thus making the lens substrate slightly opaque. This results in the disadvantage that the applicable materials for the the intraocular implant lens substrate are very limited.

SUMMARY OF THE INVENTION

An object of the present invention is to eliminate the disadvantages as stated above, to provide an intraocular implant having a good adhesion between the lens substrate and coating layer and also having a superior durability.

The intraocular implant of the present invention comprises a substrate and a coating layer with an adhesion layer provided therebetween, the adhesion layer comprising at least one member selected from the group consisting of;

(a) a hydrocarbon compound;
(b) a halogenated hydrocarbon compound;
(c) a hetero-element-containing hydrocarbon compound;
(d) an organic metal compound; and
(e) an organosilane compound.

DETAILED DESCRIPTION OF THE PREFERRED EMBODIMENTS

Figure 1:
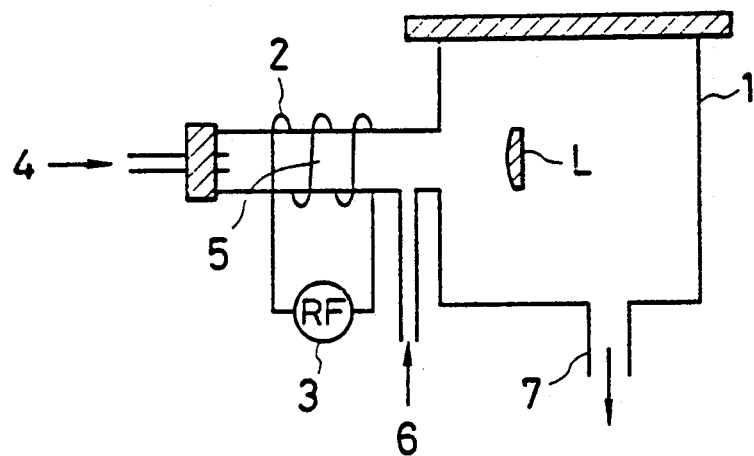
FIG. 1 is a side elevation to show an example of a plasma polymerization apparatus used in preparing the intraocular implant of the present invention.

The intraocular implant of the present invention comprises a lens substrate and a coating layer with an adhesion layer therebetween. As the lens substrate of a lens, conventionally known intraocular implants can be used as they are. Materials for the lens substrate include, for example, PMMA, HEMA, silicone resins, and transparent polyurethane resins. Of these, the intraocular implant of the present invention can be particularly effective when the silicone resins are used as the lens substrate.

Materials for the adhesion layer include saturated or unsaturated hydrocarbon compounds, aromatic hydrocarbon compounds, halogenated hydrocarbon compounds, other hetero-element-containing hydrocarbon compounds, organosilane compounds and various organic metal compounds, and at least one member selected from the above compounds is applicable. Particularly preferred are unsaturated hydrocarbon compounds, unsaturated aromatic compounds and unsaturated silicone compounds which are capable of being plasma-polymerized using a low discharge electric power.

Materials for the adhesion layer more specifically include, for example, saturated hydrocarbon compounds such as methane, ethane, propane, butane, pentane, hexane and cyclohexane; unsaturated hydrocarbon compounds such as ethylene, propene, butene, pentene and cyclohexene; aromatic hydrocarbon compounds such as styrene, benzene and toluene; heteroelement-containing compounds such as N-vinylpyrrolidone; organosilane compounds such as vinyltrimethoxysilane, tetramethoxysilane, hexamethyldisiloxane, hexamethyldisilazane, tetramethylsilane and diemthyldimethoxysilane; organic metal compounds such as tetramethyltin; and halogenated hydrocarbon compounds such as chlorotrifluoroethylene.

Materials for the coating layer provided on the adhesion layer include hydrophilic materials as exemplified by nitro compounds such as acetonitrile, N-vinylpyrrolidone, nitroethane, nitropropane and nitroisopropane; amino compounds such as acetamine, benzylamine and triethylamine; and other oxygen-containing compounds such as ethylene glycol, hydroxyethyl methacrylate, isopropyl alcohol and ethyl alcohol.

Materials for an ultraviolet light screening coating layer include nitrogen-containing compounds such as acetonitrile, azomethane and nitrobutane in the case when the coating layer is formed by plasma polymerization; and compounds such as anthracene in the case when it is similarly formed by vacuum deposition. Materials for an anti-dissolving coating layer include, for example, halogenated hydrocarbon compounds such as chlorotrifluoroethylene.

Materials for a wear resistance coating layer include, for example, 2-pyrrolidone, tetramethoxysilane, hexamethyldisiloxane and tetramethyltin.

The intraocular implant of the present invention is constituted by providing the adhesion layer on the surface of the lens substrate, and laminating on the surface of this adhesion layer the coating layer having the prescribed functions, provided that it is required to provide a hydrophilic coating layer on the outermost surface instances in where a plurality of coating layers having various functions are laminated. For example, the adhesion layer, the anti-dissolving coating layer, the ultraviolet light screening coating layer, the wear resistance coating layer and the hydrophilic coating layer are laminated in this order from the lens substrate side.

In the present invention, the adhesion layer and coating layers may preferably be formed of a plasma-polymerized film using monomer gases of the above compounds.

The plasma polymerization in the present invention can be carried out by using, for example, a plasma polymerization apparatus as illustrated in FIG. 1. On a smaller diameter section associated with a chamber 1, coil 2 is wound, and an electric current is flowed from an RF electric source 3 to generate discharge. Next, feeding inert gas as exemplified by argon gas from a carrier gas feed pipe 4 provided at an end of the small diameter section where coil 2 is wound, radicals are allowed to generate radicals at a discharge area 5 inside the small diameter section, and a monomer gas introduced thereinto from a monomer gas feed pipe 6 provided downstream in the vicinity thereof is activated by virtue of the above radicals. The carrier gas is introduced into a reaction vessel 10 so that the dissociation of the monomer gas can be suppressed. Polymers serving as the adhesion layer and coating layer are thus formed on the surface of a lens substrate L supported inside a large diameter section of the chamber 1, located most downstream. The numeral 7 denotes an exhaust vent connected to a vacuum pump (not shown). Here, the film formation of the respective plasma-polymerized films may preferably be carried out under conditions falling within the range as shown in Table 1 below.

TABLE 1

|   | Pressure (Torr) | RF power (W) | Carrier gas flow rate (SCCM) | Monomer gas flow rate (SCCM) | Film thickness (Å) | Treatment time (min) |
|---|---|---|---|---|---|---|
| A: | 1 mm~10 | <30 | 0~50 | 0.2~100 | 10~1,000 | <20 |
| B: | " | 1~300 | " | " | 50~30,000 | 1~120 |
| C: | " | " | " | " | " | " |
| D: | " | " | " | " | " | " |
| E: | " | " | " | " | " | " |

Figure 2:
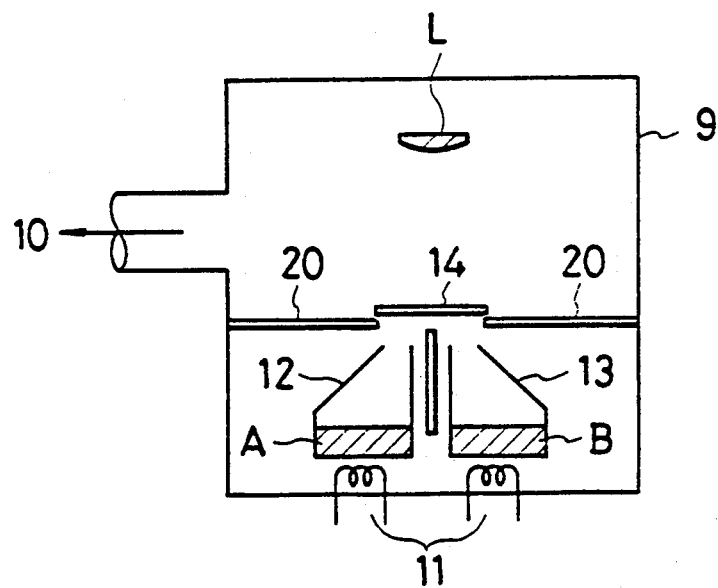
FIG. 2 is a side elevation of a vacuum deposition apparatus used in preparing the intraocular implant of the present invention.

A: Adhesion layer
B: Hydrophilic coating layer
C: Ultraviolet light screening coating layer
D: Anti-dissolving coating layer
E: Wear resistance coating layer FIG. 2 schematically illustrates a vacuum deposition apparatus used in forming the coating layers in the present invention. In FIG. 2, provided to chamber 9 is an exhaust vent 10 connected to a vacuum pump (not shown), and heating vessels 12 and 13 having heaters 11 are constructed inside the chamber 9, where the organic monomers A and B are put in the heating vessels 12 and 13, respectively, and brought into gaseous state at an upper zone of the heating vessels 12 and 13.

In this vacuum deposition apparatus, when the coating layer is formed on the lens substrate L, the inside of the chamber is evacuated to a vacuum of, for example, $5 \times 10^{-4}$ Torr or less and heated to a temperature high enough to vaporize the monomers. Thereafter, shutter 14 provided at the upper part of the openings of the heating vessels 12 and 13 is opened to allow the vapor of the organic monomers to rise up to the lens substrate L. The numeral 20 denotes a partition wall.

EXAMPLES

The present invention will be described below in more detail by referring to Examples, but the scope of a right on the present invention is by no means restricted by these Examples.

EXAMPLE 1

A silicone resin, more specifically dimethyl polysiloxane, was poured between two sheets of flat glass sheets to form a silicone rubber sheet with a thickness of 1 mm, followed by cutting into a size of 20×40 mm to obtain a test piece, on which the following film formation was carried out and thereafter evaluation was made on various items.

The above test piece was held in the plasma polymerization apparatus as illustrated in FIG. 1, at the position where the lens substrate L is supported, more specifically a position 200 mm distant from the end of the discharge zone, and the inside of the chamber 1 was evacuated to about $5 \times 10^{-6}$ Torr. Thereafter, argon gas was fed from the carrier gas feed pipe 4 and the internal pressure was set to about 1 Torr. Subsequently, the flow rate of argon was precisely set to 10 SCCM using a mass flow controller. Thereafter, ethylene monomers whose flow rate was controlled to be 2.5 SCCM using a mass flow controller were fed from the monomer feed pipe 6, and a valve (not shown) provided to the exhaust vent 7 was operated to set the internal pressure of the chamber 1 to 0.13 Torr. Next, an RF power of 30 W was applied to the coil 2 from the RF electric source 3 to generate glow discharge, which was kept for 10 minutes to form an ethylene plasma-polymerized film on the test piece to provide thereon the adhesion layer.

Subsequently the feeding of the argon gas and ethylene monomers were stopped, the exhaust valve was opened to its full width, the internal pressure of the chamber was reduced to 1 mm Torr or less, and then the exhaust valve was closed to inject argon gas into the chamber until its internal pressure came to be about 1 Torr. Thereafter the exhaust valve was again opened to its full width to sufficiently purge the inside of the system. Next, the gas flow rate of argon was precisely set to 10 SCCM using a mass flow controller, and thereafter acetonitrile monomers heated and vaporized in a heating vessel separately provided were fed from the monomer feed pipe 6 at a flow rate of 5 SCCM through a needle valve. On this occasion, a ribbon heater was used to heat the whole of a change-over valve for changing monomer gases and the path through which the acetonitrile monomers were introduced into the chamber 1.

Next, the exhaust valve was operated to control the inside of the chamber 1 to be 0.16 Torr, followed by applying an RF power of 100 W to the coil 2 to carry out film formation for 20 minutes to provide a hydrophilic acetonitrile plasma-polymerized film on the test piece.

After the film formation, the inside of the chamber 1 was sufficiently purged with argon and was subjected to atmosphere leak to restore the inside to normal pressure before the test piece was taken out. The film thickness, hydrophilic nature and changes with time, of the hydrophilic nature of the adhesion layer and coating layer thus formed were evaluated using ALPHA-STEP (manufactured by TENCOR) and based on the contact angle to water measured by a contact angle meter, respectively, and the following results are obtained.

| Film thickness: | |
| --- | --- |
| Ethylene adhesion layer | about 250 Å |
| Acetonitrile hydrophilic layer | about 400 Å |
| Contact angle (C.A.): | |
| Initial | 58° |
| After 200 days | 60° |

It was confirmed from the above results that the surface was made hydrophilic when compared with C. A.=120° of silicone rubber, and also confirmed from the value C. A. =60° after 200 days that a sufficiently durable hydrophilic surface was obtained.

EXAMPLE 2

Example 1 was repeated to form the adhesion layer and coating layer on the silicone rubber sheet, except that the adhesion layer was formed using methane monomers, the internal pressure in carrying out film formation was set to 0.05 Torr, the flow rate of argon on that occasion was set to 5 SCCM, and the film formation was carried out for 15 minutes. For the resulting test piece, the initial value of the contact angle to water and the value thereof after it was allowed to stand indoors for 200 days were determined to obtain the results as shown in Table 2.

EXAMPLE 3

Example 1 was repeated to prepare the test piece, except that a PMMA injection material was used as the substrate. For the resulting test piece, the initial value of the contact angle to water and the value thereof after it was allowed to stand indoors for 200 days were determined to obtain the results as shown in Table 2.

EXAMPLE 4

Example 1 was repeated to carry out the plasma polymerization treatment, except that the formation of the hydrophilic film was carried out using N-vinylpyrrolidone as the monomers, under conditions of an internal pressure of the chamber 1, of 0.02 Torr, an RF power of 150 W, an argon flow rate of 2 SCCM, a monomer flow rate of 5 SCCM, and a film formation time of 5 minutes. For the resulting test piece, the initial value of the contact angle to water and the value thereof after it was allowed to stand indoors for 200 days were determined, and the initial value of its light transmittance at 350 nm and the value thereof after it was allowed to stand indoors for 150 days were further determined using a spectrophotometer (U-3400, manufactured by Hitachi Ltd.; the same applies hereinafter). Results obtained are shown in Table 2.

EXAMPLE 5

In the same manner as Example 1, an adhesion layer was formed, and a plasma-polymerized film was prepared thereon using allylamine monomers under conditions of an internal pressure of 0.2 Torr, an argon carrier gas flow rate of 10 SCCM, a monomer flow rate of 10 SCCM, an RF power of 70 W, and a film formation time of 30 minutes to provide an ultraviolet-absorbing layer. For the resulting test piece, the initial value of the contact angle to water and the value thereof after it was allowed to stand indoors for 200 days were determined, and the light transmittance at 350 nm were further determined using a spectrophotometer. Results obtained are shown in Table 2.

EXAMPLE 6

In the same manner as Example 1, an adhesion layer was formed and thereafter anthracene was used to vaporize it at 150° C. in the vacuum deposition apparatus as illustrated in FIG. 2, thus providing thereon an ultraviolet-absorbing layer. For the resulting test piece, the light transmittance at 350 nm was determined using a spectrophotometer. Results obtained are shown in Table 2.

Comparative Example 1

On a test piece corresponding to the silicone resin sheet formed in Example 1, the initial contact angle to water and the light transmittance at 350 nm were measured. Results obtained are shown in Table 2.

EXAMPLE 7

Example 1 was repeated to prepare the test piece, except that, in place of the adhesion layer of Example 1, perfluorobutene monomers were formed into a film (under conditions of a monomer flow rate of 10 SCCM, a pressure in carrying out the film formation, of 0.1 Torr, and a film formation time of 20 minutes; other conditions were the same as Example 1) to provide an adhesion layer. For the resulting test piece, the initial value of the contact angle to water and the value thereof after it was allowed to stand indoors for 200 days were determined. Results obtained are shown in Table 2.

EXAMPLE 8

Example 1 was repeated to prepare the test piece, except that, in place of the adhesion layer of Example 1, N-vinylpyrrolidone monomers were formed into a film (under conditions of a pressure in carrying out the film formation, of 0.07 Torr, and an argon flow rate of 5 SCCM; other conditions were the same as Example 1) to provide an adhesion layer. For the resulting test piece, the initial value of the contact angle to water and the value thereof after it was allowed to stand indoors for 200 days were determined. Results obtained are shown in Table 2.

EXAMPLE 9

Example 1 was repeated to prepare the test piece, except that, in place of the adhesion layer of Example 1, tetradmethyltin monomers were formed into a film (under conditions of a monomer flow rate of 0.5 SCCM, an argon flow rate of 10 SCCM, a pressure in carrying out the film formation, of 0.2 Torr, and a discharge electric power of 10 W; other conditions were the same as Example 1) to provide an adhesion layer. For the resulting test piece, the initial value of the contact angle to water and the value thereof after it was allowed to stand indoors for 200 days were determined. Results obtained are shown in Table 2.

EXAMPLE 10

Example 1 was repeated to prepare the test piece, except that, in place of the adhesion layer of Example 1, tetramethoxysilane monomers were formed into a film (under conditions of a monomer flow rate of 0.5 SCCM, an argon flow rate of 10 SCCM, a pressure in carrying out the film formation, of 0.12 Torr, and a discharge electric power of 10 W; other conditions were the same as Example 1) to provide an adhesion layer. For the resulting test piece, the initial value of the contact angle to water and the value thereof after it was allowed to stand indoors for 200 days were determined. Results obtained are shown in Table 2.

TABLE 2

|  | Contact angle to water (degree) | | Light transmittance at 350 nm (%) | |
| --- | --- | --- | --- | --- |
|  | Initial value | Value after 200 days | Initial value | Value after 150 days |
| Example: | | | | |
| 1 | 58 | 60 | — | — |
| 2 | 57 | 58 | — | — |
| 3 | 58 | 61 | — | — |
| 4 | 35 | 37 | 74 | 74 |
| 5 | 38 | 41 | 71 | — |
| Comparative Example: | | | | |
| 1 | 120 | — | 92 | — |
| Example: | | | | |
| 7 | 49 | 57 | — | — |
| 8 | 42 | 55 | — | — |
| 9 | 52 | 61 | — | — |
| 10 | 39 | 45 | — | — |

As described in the above, the intraocular implant of the present invention comprises the adhesion layer provided by film formation prior to the application of the coating layers having various functions, thus bringing about the following advantages.

(1) It becomes possible to realize an intraocular implant having a superior durability, having various functions, and suitable for permanently fitting it.

(2) It becomes possible to realize an intraocular implant endowed with high functions, even by use of plastic materials having a poor adhesion and an inferior plasma resistance, which makes it possible to expand the range for the selection of materials and provide intraocular implants in an expanded variety.

(3) Because of the improved durability and wear resistance of the various functional coating layers, the products can be handled with ease in implantation, bringing about an increase in the percentage of success in the surgery.

We claim:

1. An intraocular implant comprising:
   a lens substrate;
   a coating layer formed of a first material; and
   an adhesion layer disposed between said lens substrate and said coating layer, said adhesion layer comprising a second material different from said first material, said second material having at least one compound selected from the group consisting of:
   (a) a hydrocarbon compound;
   (b) a halogenated hydrocarbon compound;
   (c) a hetero-element-containing hydrocarbon compound.
   (d) an organic metal compound; and
   (e) an organosilane compound.

2. The intraocular implant according to claim 1, wherein said lens substrate comprises polymethyl methacrylate, hydroxyl methacrylate, a silicone resin, or a polyurethane resin.

3. The intraocular implant according to claim 1, wherein said adhesion layer is a plasma-polymerized film.

4. The intraocular implant according to claim 3, wherein said coating layer is a plasma-polymerized film.

5. The intraocular implant according to claim 3, wherein said coating layer is a vacuum deposition film.

6. The intraocular implant according to claim 1, wherein said coating layer is a hydrophilic coating layer.

7. The intraocular implant according to claim 1, wherein said coating layer is an ultraviolet light screening coating layer.

8. The intraocular implant according to claim 1, wherein said coating layer is an anti-dissolving coating layer.

9. The intraocular implant according to claim 1, wherein said coating layer is a wear resistance ocoating layer.

* * * * *

UNITED STATES PATENT AND TRADEMARK OFFICE
CERTIFICATE OF CORRECTION

PATENT NO. : 5,007,928
DATED : April 16, 1991
INVENTOR(S) : MORIYUKI OKAMURA, ET AL.

It is certified that error appears in the above-identified patent and that said Letters Patent is hereby corrected as shown below:

On the title page:

IN [56] REFERENCES CITED

U.S. PATENT DOCUMENTS, "Vensen" should read --Jensen--.

COLUMN 1

Line 2, "cl BACKGROUND OF THE INVENTION" should be deleted.
Line 3, Insert --BACKGROUND OF THE INVENTION--.
Line 12, "restraining" should read --restoring--.

COLUMN 3

Line 43, "instances in" should read --in instances--.

COLUMN 7

TABLE 2, "5   38   41   71   —"   should read

--  5   38   41   71   —
    6   —    —    62   —  --.

UNITED STATES PATENT AND TRADEMARK OFFICE
CERTIFICATE OF CORRECTION

PATENT NO. : 5,007,928
DATED : April 16, 1991
INVENTOR(S) : MORIYUKI OKAMURA, ET AL.

It is certified that error appears in the above-identified patent and that said Letters Patent is hereby corrected as shown below:

COLUMN 8

Lines 41-42, "compound." should read --compound;--.
Line 66, "ocoating" should read --coating--.

Signed and Sealed this

Twenty-fourth Day of November, 1992

Attest:

DOUGLAS B. COMER

Attesting Officer

Acting Commissioner of Patents and Trademarks